United States Patent [19]

Ferrand et al.

[11] 4,104,390
[45] Aug. 1, 1978

[54] THIENO [2,3-c] AND [3,2-c] PYRIDINES

[75] Inventors: Gérard Ferrand, Lyon; Daniel Fréhel; Jean-Pierre Maffrand, both of Toulouse, all of France

[73] Assignee: Parcor, Paris, France

[21] Appl. No.: 808,694

[22] Filed: Jun. 21, 1977

[30] Foreign Application Priority Data

Jul. 13, 1976 [FR] France .................. 76 21440

[51] Int. Cl.² .................. C07D 513/04; A61K 31/38
[52] U.S. Cl. .................. 424/256; 260/294.8 C
[58] Field of Search .................. 260/294.8 C; 424/256

[56] References Cited

FOREIGN PATENT DOCUMENTS 1,812,404  8/1969  Fed. Rep. of Germany .... 260/294.8 C
2,004,816  8/1970  Fed. Rep. of Germany .... 260/294.8 C

*Primary Examiner*—John M. Ford
*Attorney, Agent, or Firm*—Young & Thompson

[57] ABSTRACT

This invention relates to pyridine derivatives of the formulae:

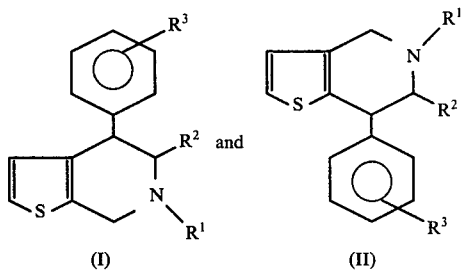

in which $R^1$ is hydrogen, lower alkyl, aralkyl optionally substituted on the aromatic nucleus with at least a halogen atom or a hydroxy, nitro, amino, cyano, carboxy, alkoxycarbonyl, lower alkyl, lower alkoxy or trifluoromethyl group; $R^2$ is hydrogen or lower alkyl; and $R^3$ is hydrogen or at least a substituent selected from a halogen atom, a hydroxy, lower alkyl and lower alkoxy group, and their pharmaceutically acceptable inorganic or organic acid addition salts.

Said compounds have particularly an anti-inflammatory and blood-platelet aggregation inhibiting activity.

5 Claims, No Drawings

THIENO [2,3-c] AND [3,2-c] PYRIDINES

This invention relates to new thienopyridine derivatives, to a process for their preparation, and to their applications in human and veterinary medicine.

The new compounds of this invention have the following general formulae:

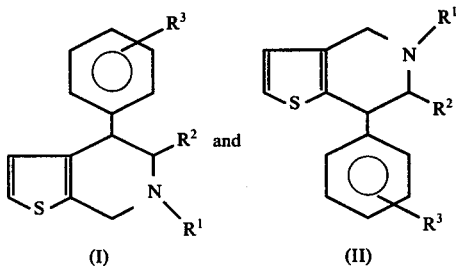

in which:
- R¹ represents a hydrogen atom, a lower alkyl group, an aralkyl group optionally substituted on the aromatic nucleus with at least a halogen atom or a hydroxy, nitro, amino, cyano, carboxy, alkoxycarbonyl, lower alkyl, lower alkoxy or trifluoromethyl group;
- R² represents a hydrogen atom or a lower alkyl group; and
- R³ represents a hydrogen atom or at least a substituent selected from a halogen atom, a hydroxy, lower alkyl and lower alkoxy group.

In the above formulae, the lower alkyl and alkoxy groups contain 1–6 carbon atoms.

The invention includes also within its scope the inorganic or organic acid addition salts and the quaternary ammonium derivatives of the compounds of the formula (I) or (II).

This invention relates also to a process for the preparation of compounds of the formula (I) or (II), comprising cyclizing compounds of the formula (III) or (IV), respectively,

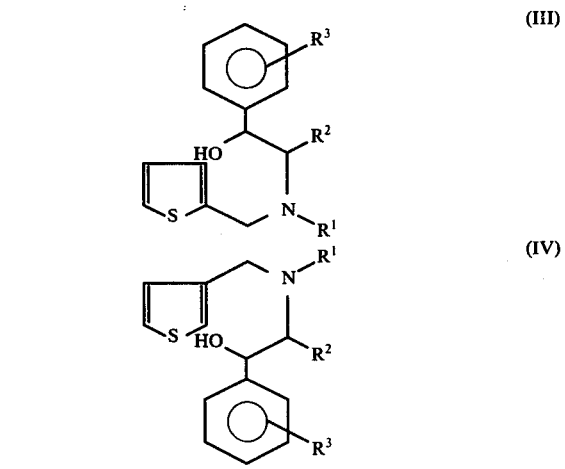

by heating in acidic medium.

This cyclization reaction is effected in polyphosphoric acid or 50% sulfuric acid at temperatures between 50° and 100° C.

Compounds (III) and (IV), used as intermediates, have never been described in the literature, but are prepared according to conventional methods. Compounds (III), for example, may be obtained by one of the following methods:

(a) reaction of a phenyl-ethanolamine of the formula (V) in which R² and R³ have the above-defined meanings, either with 2-thienaldehyde, followed by hydrogenation, or with a 2-halomethylthiophene, to give compound (IIIa) which is then condensed with a halide R¹X in which R¹ has the above-defined meaning and X is a halogen atom (chlorine, bromine or iodine), when it is desired that R¹ be other than a hydrogen atom.

The reaction scheme defined in (a) is as follows:

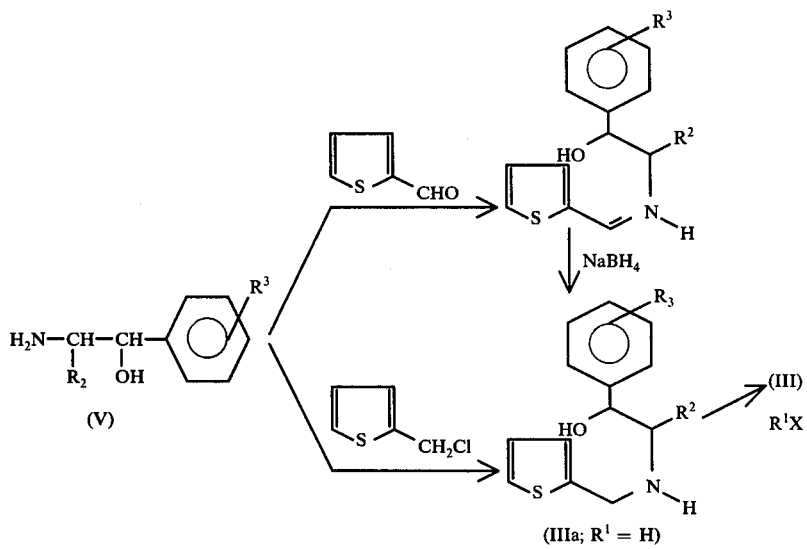

(b) reaction of a primary amine R¹-NH₂ in which R¹ has the above-defined meaning, either with 2-thienaldehyde followed by a hydrogenation, or with a 2-halomethyl-thiophene, the resulting compound being then condensed either with an α-haloketone of the formula (VI) in which R² and R³ have the above-defined meanings, and then hydrogenated, or with a styrene oxide of the formula (VII) in which $R^3$ has the above-defined meaning, according to the following reaction scheme:

The same methods applied to 3-thienaldehyde or 3-bromomethyl-thiophene lead to corresponding compounds (IV). Intermediates (V) and (VI) are commercially available products, or are described in the literature.

Compounds (I) and (II) in which $R^1$ is other than hydrogen may also be obtained by condensation of corresponding compounds (I) and (II) in which $R^1$ is hydrogen, with a halide $R^1X$. The reaction is effected within an inert solvent such as ethanol or dimethylformamide, in the presence of a base such as potassium carbonate. When X is chlorine or bromine, a catalytically effective amount of an inorganic iodide such as potassium iodide is advantageously added.

The following non limiting Examples illustrate the invention.

EXAMPLE 1:
5-Methyl-4-phenyl-4,5,6,7-tetrahydro-thieno[2,3-c]pyridine (derivative No. 1)

(a) preparation of aminoalcohol (III) ($R^1 = R^3 = H$; $R^2 = CH_3$)

A mixture of 2-thienaldehyde (11.9 g; 0.106 mole), norephedrine hydrochloride (20 g; 0.106 mole), triethylamine (10.7 g; 0.106 mole) in dry ethanol (250 ml) is stirred at room temperature during a period of time of 5 hours. Sodium borohydride (4.5 g; 0.115 mole) is added portionwise thereto, and the resulting material is left aside overnight at room temperature. Excess sodium borohydride is destroyed by addition of acetone and the mixture is evaporated to dryness. The residue is taken up into water and extracted with methylene chloride. The organic extracts are dried over sodium sulfate, filtered through a silica bed and evaporated to dryness. The residual oil, which consists of aminoalcohol (III) ($R^1 = R^3 = H$; $R^2 = CH_3$) crystallizes on standing (M.p. = 50° C; 21.9 g; yield: 82%). The hydrochloride is recrystallized from isopropanol. M.p. = 184° C.

(b) cyclization of the aminoalcohol

A mechanically stirred mixture of the preceding aminoalcohol (23 g; 0.093 mole) in commercial polyphosphoric acid (100 g) is heated at 60° C, for 1 hour, under a nitrogen atmosphere. After cooling, the reaction mixture is poured over ice, made basic with concentrated aqueous ammonia and extracted with methylene chloride.

The organic extracts are dried over sodium sulfate, filtered through a silica bed and evaporated to dryness. The residual oil is converted to the hemifumarate which is then recrystallized from methanol-water. (M.p. = 202° C; 13.4 g; Yield: 39%).
Hydrochloride: M.p. = 236° C (isopropanol-ether).

EXAMPLE 2:
6-Methyl-7-phenyl-4,5,6,7-tetrahydro-thieno[3,2-c]pyridine (derivative No. 2)

(a) preparation of aminoalcohol (IV)($R^1 = R^3 = H$; $R^2 = CH_3$)

The preparation is effected from 3-thienaldehyde and norephedrine, according to the procedure described in Example 1a.
Hydrochloride: M.p. = 204° C (ethanol); Yield: 57%.

(b) cyclization of the aminoalcohol

The cyclization is effected according to the procedure described in Example 1b.
Base: M.p. = 78° C (hexane); yield: 66%.

EXAMPLE 3:
4-Phenyl-4,5,6,7-tetrahydro-thieno[2,3-c]pyridine (derivative No. 3)

(a) preparation of aminoalcohol (III) ($R^1 = R^2 = R^3 = H$)

The aminoalcohol is prepared from 2-thienaldehyde and 2-amino-1-phenyl-ethanol, according to the procedure of Example 1a.
Base: M.p. = 74° C (cyclohexane); yield: 66%.

(b) cyclization of the aminoalcohol

Cyclization of the aminoalcohol is effected according to the procedure described in Example 1b.
Methane sulfonate: M.p. = 200° C (ethanol-isopropanol); yield: 57%.

EXAMPLE 4
7-Phenyl-4,5,6,7-tetrahydro-thieno[3,2-c]pyridine (derivative No. 4)

(a) preparation of aminoalcohol (IV) ($R^1 = R^2 = R^3 = H$)

The aminoalcohol is prepared from 3-thienaldehyde and 2-amino-1-phenyl-ethanol, according to the procedure of Example 1a.
Base: M.p. = 90° C (cyclohexane); yield: 84%

(b) cyclization of the aminoalcohol

It is effected according to the procedure of Example 1b.
Methanesulfonate: M.p. = 230° C; Yield: 51%.

EXAMPLE 5:
6-Methyl-4-phenyl-4,5,6,7-tetrahydro-thieno[2,3-c]pyridine (derivative No. 5)

(a) preparation of aminoalcohol (III) ($R^1 = CH_3$; $R^2 = R^3 = H$)

The N-methylation of aminoalcohol (III) ($R^1 = R^2 = R^3 = H$) described in Example 3 is effected by the Leuckart reaction (heating in the presence of formalin and formic acid).
Maleate: M.p. = 94° C (ethanol); yield: 93%.

(b) cyclization of the aminoalcohol

Cyclization of the aminoalcohol is effected according to the procedure of Example 1b. Hydrochloride: M.p. = 214° C(isopropyl ether-ethanol; Yield: 53%.

EXAMPLE 6:
5-Methyl-7-phenyl-4,5,6,7-tetrahydro-thieno[3,2-c]pyridine (derivative No. 6)

(a) preparation of aminoalcohol (IV) ($R^1 = CH_3$; $R^2 = R^3 = H$)

The N-methylation of aminoalcohol (IV) ($R^1 = R^2 = R^3 = H$) described in Example 4 is effected by the Leuckart reaction (heating in the presence of formalin and formic acid).
Base: M.p. = 68° C (cyclohexane); Yield: 84%.

(b) cyclization of the aminoalcohol

Cyclization of the aminoalcohol is effected according to the procedure of Example 1b. Fumarate: M.p. = 195° C (water); Yield: 41%.

EXAMPLE 7:
6-o-Chlorobenzyl-4-p-methoxyphenyl-4,5,6,7-tetrahydro-thieno[2,3-c]pyridine (derivative No. 7)

(a) preparation of aminoalcohol (III) ($R^1 = $ o.Cl—$C_6H_4$—$CH_2$; $R^2 = H$; $R^3 = $ p.$OCH_3$)

A mixture of 2-thienaldehyde (29 g; 0.26 mole) and o-chlorobenzylamine (36.8 g; 0.26 mole) in benzene (300 ml) is refluxed for 3 hours in a flask provided with a Dean-Stark water separator and an overhead cooling device. The solution is evaporated to dryness and the residue is dissolved in ethanol (250 ml). Sodium borohydride (10.1 g; 0.26 mole) is added thereto portionwise and the reaction mixture is allowed to stand overnight at room temperature. Excess reducing agent is destroyed by addition of acetone and the mixture is then evaporated to dryness. The residue is taken up into 1N hydrochloric acid and extracted with ether. The aqueous phase is made basic with 2N sodium hydroxide and extracted with ether. The ether extracts are washed with water, filtered through a silica bed and evaporated to dryness, to give 49 g (Yield: 80%) N-(2-thienyl)-methyl-o.chlorobenzylamine (oxalate: M.p. = 220° C) as an oil which is used directly in the subsequent step.

A mixture of the preceding amine (16.5 g; 0.069 mole) and α-bromo-p.methoxyacetophenone (7.85 g; 0.0345 mole) in dry benzene (120 ml) is refluxed during a period of time of 15 hours. After cooling, the precipitate consisting of the hydrobromide of the starting amine is filtered off, and the filtrate is evaporated to dryness. The residue is dissolved in ether, filtered through a silica bed and evaporated to dryness. To a solution of the resulting residual oil (10 g; 75%) in ethanol (100 ml) is added portionwise 1.3 g (0.0345 mole) sodium borohydride, and the reaction mixture is then allowed to stand overnight at room temperature. Excess reducing agent is destroyed by addition of acetone and the solution is evaporated to dryness. The residue is taken up into water and extracted with methylene chloride. The organic extracts are washed with water, filtered through a silica bed and evaporated to dryness, to give 7.2 g (yield: 54%) of the desired aminoalcohol (III), as an oil. Overall yield of the three steps: 32%.

(b) cyclization of the aminoalcohol

Cyclization of the aminoalcohol is conducted according to the procedure described in Example 1b: the resulting product is isolated as the fumarate: M.p. = 110° C (isopropanol-ethanol); Yield: 72%.
Hydrochloride: M.p. = 120° C.

EXAMPLE 8:
6-o.Cyanobenzyl-4-phenyl-4,5,6,7-tetrahydro-thieno[2,3-c]pyridine (derivative No. 8)

A mixture of 4-phenyl-4,5,6,7-tetrahydro-thieno[2,3-c]pyridine (6 g; 0.028 mole) (Example 3), o.cyanobenzyl bromide (5.9 g; 0.03 mole) and solid potassium carbonate (5.8 g; 0.042 mole) in dimethylformamide (100 ml) is heated at 70° C during 2 hours. After cooling, the precipitate is filtered and the solvent is evaporated off under reduced pressure. The residue is taken up into water and extracted with ether. The organic extracts are washed with water, dried over sodium sulfate, filtered through a silica bed and evaporated to dryness. The residue is recrystallized from cyclohexane: M.p. = 124° C (Yield: 67%).

EXAMPLE 9:
6-o.Chlorobenzyl-4-p.chlorophenyl-4,5,6,7-tetrahydro-thieno[2,3-c]pyridine (derivative No. 9)

(a) preparation of aminoalcohol (III) ($R^1 = $ o.Cl—$C_6H_4$—$CH_2$; $R^2 = H$; $R^3 = $ p.Cl)

Aminoalcohol (III) is prepared by condensation of N(2-thienyl)methyl-o.chlorobenzylamine with α-bromo-p.chloroacetophenone and reduction of the resulting aminoketone with sodium borohydride, according to the procedure of Example 7a.
Hydrochloride: M.p. = 178° C (isopropanol); Yield: 74%.

(b) Cyclization of the aminoalcohol

Cyclization of the aminoalcohol is effected according to the procedure of Example 1b. Hydrochloride: M.p. = 180° C (ethanolisopropanol); Yield: 49%.

EXAMPLE 10:
6-o.Chlorobenzyl-4-p.tolyl-4,5,6,7-tetrahydro-thieno[2,3-c]pyridine (derivative No. 10)

(a) preparation of aminoalcohol (III) ($R^2 = $ o.Cl—$C_6H_4$—$CH_2$; $R^2 = H$; $R^3 = $ p.$CH_3$)

Aminoalcohol (III) is prepared by condensation of N-(2-thienyl)-methyl-o.chlorobenzylamine with α-bromo-p.methylacetophenone and reduction of the resulting aminoketone with sodium borohydride, according to the procedure of Example 7a.
Base: M.p. = 68° C (cyclohexane); Yield: 64%.

(b) cyclization of the aminoalcohol

Cyclization of the aminoalcohol is effected according to the procedure of Example 1b.

EXAMPLE 11:
6-o.Chlorobenzyl-4-phenyl-4,5,6,7-tetrahydro-thieno[2,3-c]pyridine (derivative No. 11)

o.Chlorobenzyl chloride is condensed with 4-phenyl-4,5,6,7-tetrahydro-thieno[2,3-c]pyridine (Example 3) according to the procedure of Example 8. Furmarate: M.p. = 180° C (isopropanol); Yield: 66%.

EXAMPLE 12:
6-Benzyl-4-phenyl-4,5,6,7-tetrahydro-thieno[2,3-c]pyridine (derivative No. 12)

Benzyl chloride is condensed with 4-phenyl-4,5,6,7-tetrahydro-thieno[2,3-c]pyridine (Example 3), according to the procedure of Example 8. Hydrochloride; M.p. = 185° C (isopropanol); Yield: 52%.

EXAMPLE 13:
6-o.Fluorobenzyl-4-phenyl-4,5,6,7-tetrahydro-thieno[2,3-c]pyridine (derivative No. 13)

o.Fluorobenzyl chloride is condensed with 4-phenyl-4,5,6,7-tetrahydro-thieno[2,3-c]pyridine (Example 3) according to the procedure of Example 8. Hydrochloride: M.p. = 168° C. Yield: 24%.

EXAMPLE 14:
4-Phenyl-6-(3,4,5-trimethoxy-benzyl)-4,5,6,7-tetrahydro-thieno[2,3-c]pyridine (derivative No. 14)

3,4,5-Trimethoxy-benzyl chloride is condensed with 4-phenyl-4,5,6,7-tetrahydro-thieno[2,3-c]pyridine (Example 3), according to the procedure of Example 8. Hydrochloride: M.p. = 140° C (isopropanol-ethanol); yield: 34%.

EXAMPLE 15:
6-o.Methoxycarbonylbenzyl-4-phenyl-4,5,6,7-tetrahydro-thieno[2,3-c]pyridine (derivative No. 15)

Methyl 2-bromo-methyl-benzoate is condensed with 4-phenyl-4,5,6,7-tetrahydro-thieno[2,3-c]pyridine (Example 3), according to the procedure of Example 8. Base: M.p. = 90° C (hexane-cyclohexane); Yield: 68%.

EXAMPLE 16:
6-o.Carboxybenzyl-4-phenyl-4,5,6,7-tetrahydro-thieno[2,3-c]pyridine (derivative No. 16)

The derivative is obtained by basic hydrolysis of the compound described in the preceding Example. Hydrochloride: M.p. = 204° C (ethanol-isopropanol); Yield: 79%.

EXAMPLE 17:
6-p.Nitrobenzyl-4-phenyl-4,5,6,7-tetrahydro-thieno[2,3-c]pyridine (derivative No. 17)

p.Nitrobenzyl chloride is condensed with 4-phenyl-4,5,6,7-tetrahydro-thieno[2,3-c]pyridine (Example 3), according to the procedure of Example 8. Hydrochloride: M.p. = 168° C. Yield: 61%.

EXAMPLE 18:
4-Phenyl-6-p.tolyl-4,5,6,7-tetrahydro-thieno[2,3-c]pyridine (derivative No. 18)

p.Tolyl chloride is condensed with 4-phenyl-4,5,6,7-tetrahydro-thieno[2,3-c]pyridine (Example 3) according to the procedure of Example 8. Hydrochloride: M.p. = 196° C (acetonitrile-ethyl ether); yield: 58%.

EXAMPLE 19:
5-o.Chlorobenzyl-7-phenyl-4,5,6,7-tetrahydro-thieno[3,2-c]pyridine (derivative No. 19)

o.Chlorobenzyl chloride is condensed with 7-phenyl-4,5,6,7-tetrahydro-thieno[3,2-c]pyridine (Example 4) according to the procedure of Example 8. Hydrochloride: M.p. = 164° C (isopropanol-ethyl ether); Yield 31%.

EXAMPLE 20:
5-Phenethyl-7-phenyl-4,5,6,7-tetrahydro-thieno[3,2-c]pyridine (derivative No. 20)

Phenethyl bromide is condensed with 7-phenyl-4,5,6,7-tetrahydro-thieno[3,2-c]pyridine (Example 4) according to the procedure of Example 8. Fumarate: M.p. = 208° C (methanol-ethanol); yield: 82%.

EXAMPLE 21:
5-Butyl-7-phenyl-4,5,6,7-tetrahydro-thieno[3,2-c]pyridine (derivative No. 21)

Butyl bromide is condensed with 7-phenyl-4,5,6,7-tetrahydrothieno[3,2-c]pyridine (Example 4) according to the procedure of Example 8.
Fumarate: M.p. = 196° C (methanol); yield: 57%.

EXAMPLE 22:
6-Methyl-5-p.nitrobenzyl-7-phenyl-4,5,6,7-tetrahydro-thieno[3,2-c]pyridine (derivative No. 22)

p.Nitrobenzyl chloride is condensed with 6-methyl-7-phenyl-4,5,6,7-tetrahydro-thieno[3,2-c]pyridine (Example 2), according to the procedure of Example 8. Base: M.p. = 150° C; Yield: 66%.

EXAMPLE 23:
5-o.Chlorobenzyl-6-methyl-7-phenyl-4,5,6,7-tetrahydro-thieno[3,2-c]pyridine (derivative No. 23)

o.Chlorobenzyl chloride is condensed with 6-methyl-7-phenyl-4,5,6,7-tetrahydro-thieno[3,2-c]pyridine (Example 2), according to the procedure of Example 8. Base: M.p. = 102° C; yield: 58%.

EXAMPLE 24:
5-Benzyl-7-phenyl-4,5,6,7-tetrahydro-thieno[3,2-c]pyridine (derivative No. 24)

Benzyl chloride is condensed with 7-phenyl-4,5,6,7-tetrahydro-thieno[3,2-c]pyridine (Example 4), according to the procedure of Example 8. Fumarate: M.p. = 200° C; yield: 34%.

EXAMPLE 25:
6-Phenethyl-4-phenyl-4,5,6,7-tetrahydro-thieno[2,3-c]pyridine (derivative) No. 25)

Phenethyl bromide is condensed with 4-phenyl-4,5,6,7-tetrahydro-thieno[2,3-c]pyridine (Example 3), according to the procedure of Example 8. Base: M.p. = 110° C; yield: 59%.

EXAMPLE 26:
5-o.Cyanophenyl-7-phenyl-4,5,6,7-tetrahydro-thieno[3,2-c]pyridine (derivative No. 26)

o.Cyanobenzyl bromide is condensed with 7-phenyl-4,5,6,7-tetrahydro-thieno[3,2-c]pyridine (Example 4), according to the procedure of Example 8. Hydrochloride: M.p. = 160° C; yield: 71%.

EXAMPLE 27:
5-p.Methoxybenzyl-7-phenyl-4,5,6,7-tetrahydro-thieno[3,2-c]pyridine (derivative No. 27)

p.Methoxybenzyl chloride is condensed with 7-phenyl-4,5,6,7-tetrahydro-thieno[3,2-c]pyridine (Example 4), according to the procedure of Example 8. Hydrochloride; M.p. = 176° C; yield: 75%.

EXAMPLE 28:
5-o.Methoxycarbonylbenzyl-7-phenyl-4,5,6,7-tetrahydro-thieno[3,2-c]pyridine (derivative No. 28)

Methyl 2-bromomethyl benzoate is condensed with 7-phenyl-4,5,6,7-tetrahydro-thieno[3,2-c]pyridine (Example 4), according to the procedure of Example 8. Base: M.p. = 114° C; Yield: 65%.

The results of toxicological and pharmacological investigations reported below demonstrate the useful activities of the derivatives of the formula (I) and (II), particularly their blood-platelet aggregation inhibiting and anti-inflammatory activities.

Thus, the invention includes also within its scope a therapeutic composition having particularly blood-platelet aggregation inhibiting and anti-inflammatory activities, comprising, as active ingredient, an efficient amount of a derivative of the formula (I) and (II) or a pharmaceutically acceptable acid addition salt thereof, optionally together with pharmaceutically acceptable carriers or excipients.

I — TOXICOLOGICAL INVESTIGATION

The compounds of the formula (I) and (II) benefit from an excellent tolerance and a low toxicity. Thus, the $LD_{50}/24$ hrs/kg of body weight of the animal, determined in mice according to the method of Miller and Tainter for the oral route is in excess of 700 mg for all derivatives.

By the intravenous route, the $LD_{50}$ determined in mice were, for example, 63 mg with derivative 1, 69 mg with derivative 3 and 61 mg with derivative 5.

In addition, the tests carried out on acute, chronic, subchronic and delayed toxicity in various animal species failed to demonstrate any local or systemic reaction, any perturbation in the regularly effected biological control tests, any anomaly in the microscopical and macroscopical examinations carried out in the animals sacrificed and autopsied at the end of the experimentation.

II — PHARMACOLOGICAL INVESTIGATION

(1) Blood-platelet aggregation inhibiting action

Blood is taken from the jugular vein of Wistar rats. From this citrated blood, and after centrifugation, is reconstituted a plasma containing 600,000 ± 20,000 blood-platelets per ml which is used in all aggregation determinations.

(a) Determination of A.D.P.-induced blood-platelet aggregation 0.4 ml plasma is placed in a siliconized tube provided with a magnet bar, also siliconized. The tube is introduced into an aggregometer coupled with an apparatus for recording optical density variations. When light transmission has reached a stable value, 0.5 ml of a solution containing 10 μM A.D.P. (Adenosine-Di-Phosphate) is introduced into the tube.

Blood-platelet aggregation causes an increase of light transmission followed by a decrease subsequent to the deaggregation phase.

The maximal optical density variation thus determined characterizes the intensity of the aggregation.

(b) Determination of collagen-induced blood-platelet aggregation

The A.D.P. solution is substituted with a collagen solution (bovine tendon extract).

(c) Results

Different groups of 20 rats are used, each group being orally administered a test derivative at a dosage of 100 mg/kg. The results obtained in the course of both tests are reported in following Table I which gives the percent inhibition of blood-platelet aggregation obtained, with respect to the control group, 3 hours after treatment with the therapeutic composition of this invention in the A.D.P. and collagen tests.

TABLE I

| Treatment | Percent inhibition | |
|---|---|---|
| | A.D.P. | Collagen |
| derivative n°1 | 64.9 | 96.2 |
| derivative n°2 | 6.24 | 92.7 |
| derivative n°3 | 64.1 | 95.6 |
| derivative n°4 | 64.0 | 95.0 |
| derivative n°5 | 63.6 | 93.8 |
| derivative n°6 | 61.7 | 90.4 |
| derivative n°7 | 61.5 | 90.7 |
| derivative n°8 | 63.2 | 92.5 |
| derivative n°9 | 64.3 | 93.8 |
| derivative n°10 | 65.0 | 96.0 |
| derivative n°11 | 62.8 | 91.2 |
| derivative n°12 | 63.7 | 93.3 |
| derivative n°13 | 64.3 | 94.8 |
| derivative n°14 | 64.1 | 93.9 |
| derivative n°15 | 61.7 | 92.3 |
| derivative n°16 | 63.2 | 94.1 |
| derivative n°17 | 63.9 | 95.0 |
| derivative n°18 | 62.5 | 93.5 |
| derivative n°19 | 62.3 | 93.7 |
| derivative n°20 | 63.6 | 94.2 |
| derivative n°21 | 62.2 | 94.0 |
| derivative n°22 | 63.4 | 94.6 |
| derivative n°23 | 64.8 | 94.5 |
| derivative n°24 | 62.6 | 93.0 |
| derivative n°25 | 64.1 | 93.8 |
| derivative n°26 | 60.9 | 90.2 |
| derivative n°27 | 63.0 | 92.4 |
| derivative n°28 | 62.3 | 92.2 |

(2) Anti-inflammatory action

(a) Carrageenin-induced localized edema method 0.1 ml of a 1% carrageenin solution is injected in the metatarsal flexor muscles of the right hind limb of rats at time 0. The animals of the treated group are additionally orally administered 100 mg/kg of the test derivative, respectively one hour prior to injection of the phlogogenic agent, simultaneously with said injection, and then 1 hour and 2.5 hours thereafter. The determinations effected by means of a ROCH micrometer at times 0, 1 hour, 2 hours, 3 hours and 5 hours after carrageenin administration make it possible to determine, as a function of time, the percent anti-inflammatory activity with respect to the reference group.

The results obtained are set forth in Table II.

(b) Ovalbumen-induced systemic edema method

Simultaneous injection of 1 ml ovalbumen and 0.5 ml of a 1% aqueous Evans Blue solution is effected in rats. On the other hand, the animals of the treated group are administered orally 100 mg/kg of the test derivative one hour prior to ovalbumen administration and simultaneously with said administration. The intensity of the phenomenon thus induced is scored according to a scale from 1 to 5 depending on the progress of the inflammatory syndrome. The mean intensity of the edem and the percent decrease of the edema reaction with respect to the control group are thus determined as a function of time.

The percent anti-inflammatory activity obtained 2 hours and 3 hours after ovalbumen injection are reported in Table III.

TABLE II

| Derivative n° | Percent anti-inflammatory activity after | | | |
|---|---|---|---|---|
| | 1 hour | 2 hours | 3 hours | 5 hours |
| 1 | 37 | 43 | 45 | 47 |
| 2 | 42 | 48 | 51 | 54 |
| 3 | 41 | 46 | 50 | 51 |
| 4 | 38 | 44 | 49 | 53 |
| 5 | 37 | 45 | 50 | 51 |
| 6 | 45 | 52 | 56 | 58 |
| 7 | 44 | 50 | 54 | 59 |
| 8 | 42 | 49 | 53 | 56 |
| 9 | 44 | 52 | 55 | 57 |
| 10 | 38 | 45 | 48 | 52 |
| 11 | 39 | 45 | 49 | 55 |
| 12 | 47 | 53 | 57 | 60 |
| 13 | 46 | 51 | 55 | 57 |
| 14 | 37 | 44 | 49 | 54 |
| 15 | 39 | 47 | 50 | 54 |
| 16 | 39 | 45 | 50 | 52 |
| 17 | 42 | 50 | 54 | 58 |
| 18 | 40 | 48 | 53 | 56 |
| 19 | 47 | 53 | 54 | 56 |
| 20 | 43 | 48 | 52 | 55 |
| 21 | 38 | 44 | 46 | 49 |
| 22 | 41 | 49 | 53 | 56 |
| 23 | 39 | 44 | 48 | 52 |
| 24 | 41 | 47 | 50 | 53 |
| 25 | 47 | 52 | 56 | 60 |
| 26 | 44 | 49 | 52 | 56 |
| 27 | 38 | 45 | 49 | 52 |
| 28 | 41 | 47 | 51 | 53 |

TABLE III

| Derivative n° | Percent anti-inflammatory activity | |
|---|---|---|
| | after 2 hours | after 3 hours |
| 1 | 47 | 54 |
| 2 | 42 | 50 |
| 3 | 52 | 59 |
| 4 | 54 | 62 |
| 5 | 44 | 51 |
| 6 | 47 | 55 |
| 7 | 52 | 59 |
| 8 | 46 | 54 |
| 9 | 48 | 56 |
| 10 | 53 | 60 |
| 11 | 51 | 58 |
| 12 | 47 | 55 |
| 13 | 43 | 50 |
| 14 | 43 | 52 |
| 15 | 54 | 62 |
| 16 | 49 | 56 |
| 17 | 43 | 51 |
| 18 | 47 | 56 |
| 19 | 49 | 57 |
| 20 | 53 | 61 |
| 21 | 51 | 57 |
| 22 | 50 | 57 |
| 23 | 47 | 54 |
| 24 | 42 | 47 |
| 25 | 44 | 51 |
| 26 | 48 | 54 |
| 27 | 51 | 56 |
| 28 | 45 | 52 |

The results of said investigations demonstrate the low toxicity and the useful blood-platelet aggregation inhibiting and anti-inflammatory properties of the derivatives of the formula (I) and (II) which make them highly valuable in human and veterinary medicine.

The therapeutic composition of this invention may be formulated for oral administration as tablets, coated tablets, capsules, drops and syrups. It may also be formulated for rectal administration as suppositories, and, for parenteral administration, as injectable solutions.

Each unit dose contains advantageously 0.025–0.500 g active ingredient, the daily dosage regimen varying between 0.025 g to 1.00 g active ingredient according to the age of the patient and the disease treated.

Non limiting Examples of pharmaceutical formulations of the therapeutic composition of this invention are given below.

| EXAMPLE 29 - | Tablets | |
| | derivative n°1 | 0.075 g |
| | Excipient: | |
| | corn starch, alginic acid, | |
| | orange-yellow S lacquer, | |
| | magnesium stearate | |
| EXAMPLE 30 - | Coated tablets | |
| | derivative n°4 | 0.100 g |
| | Excipient: | |
| | talc, polyvinylpyrrolidone, hydroxy- | |
| | ethylcellulose, gum arabic, sugar, | |
| | titanium dioxide, glucose, white wax, | |
| | carnauba wax, lactose, tartrazine | |
| | yellow | |
| EXAMPLE 31 - | Capsules | |
| | derivative n°7 | 0.100 g |
| | Excipient: talc, corn starch, | |
| | saccharose | |
| EXAMPLE 32 - | Injectable ampoules | |
| | derivative n°8 | 0.080 g |
| | Excipient: isotonic solvent, to make | 2 ml |
| EXAMPLE 33 - | Suppositories | |
| | derivative n°10 | 0.075 g |
| | Excipient: | |
| | semi-synthetic triglycerides | |

The toxicological and pharmacological investigations reported above demonstrate the good tolerance of the derivatives of the formula (I) and (II) and their blood-platelet aggregation inhibiting and anti-inflammatory activities.

Thus, the therapeutic composition of this invention may usefully be administered to humans, for preventive or curative purposes, in the treatment of diseases which induce a pathological modification of blood-platelet aggregation, such as the thrombo-embolic diseases.

It may also be administered in the treatment of all inflammatory conditions, whatever their etiology: chronic inflammatory rheumatism, degenerative rheumatism, ab-articular diseases, inflammatory diseases of the oto-rhino-laryngologic system, in traumatology and in post-operative surgery.

Having now described our invention what we claim as new and desire to secure by Letters Patent is:

1. Pyridine derivatives having the following formulae (I) and (II):

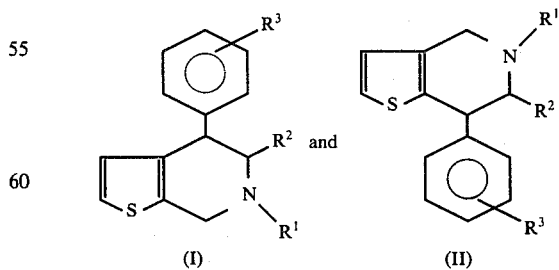

in which $R^1$ represents a radical selected from hydrogen, lower alkyl and aralkyl optionally substituted in the aromatic nucleus with at least a group selected from halogen, hydroxy, nitro, amino, cyano, carboxy, alkoxycarbonyl, lower alkyl, lower alkoxy and trifluoromethyl;

R² represents a group selected from hydrogen and lower alkyl; and

R³ represents a group selected from hydrogen and at least a substituent selected from halogen, hydroxy, lower alkyl and lower alkoxy, and their pharmaceutically acceptable inorganic and organic acid addition salts.

2. Process for the preparation of pyridine derivatives having the following formulae (I) and (II):

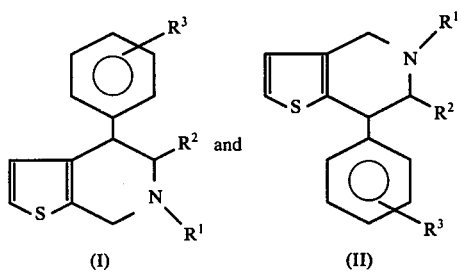

in which R¹ represents a radical selected from hydrogen, lower alkyl and aralkyl optionally substituted in the aromatic nucleus with at least a group selected from halogen, hydroxy, nitro, amino, cyano, carboxy, alkoxycarbonyl, lower alkyl, lower alkoxy and trifluoromethyl;

R² represents a group selected from hydrogen and lower alkyl; and

R³ represents a group selected from hydrogen and at least a substituent selected from halogen, hydroxy, lower alkyl and lower alkoxy, and their pharmaceutically acceptable inorganic and organic acid addition salts, comprising cyclizing a compound selected from the compounds of the formulae (III) and (IV), respectively:

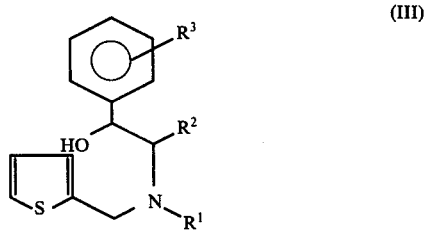

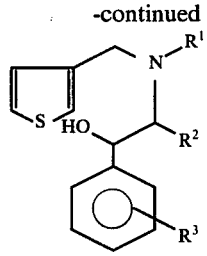

by heating in acidic medium.

3. Process as claimed in claim 2, wherein said acidic medium consists of an acid selected from polyphosphoric and 50% sulfuric acids.

4. Therapeutic composition having an anti-inflammatory and blood-platelet aggregation inhibiting activity, comprising, as active ingredient, an efficient amount of a pyridine derivative selected from the compounds having the following formulae (I) and (II):

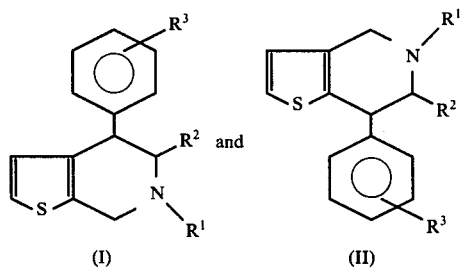

in which R¹ represents a radical selected from hydrogen, lower alkyl and aralkyl optionally substituted in the aromatic nucleus with at least a group selected from halogen, hydroxy, nitro, amino, cyano, carboxy, alkoxycarbonyl, lower alkyl, lower alkoxy and trifluoromethyl;

R² represents a group selected from hydrogen and lower alkyl; and

R³ represents a group selected from hydrogen and at least a substituent selected from halogen, hydroxy, lower alkyl and lower alkoxy, and their pharmaceutically acceptable inorganic and organic acid addition salts, together with pharmaceutically acceptable excipients.

5. Therapeutic composition as claimed in claim 4, in unit dosage form, each unit dose containing 0.025 g to 0.500 g active ingredient.

* * * * *